United States Patent [19]

Shiono

[11] Patent Number: 5,024,216

[45] Date of Patent: Jun. 18, 1991

[54] KNEE SUPPORT

[75] Inventor: Katuaki Shiono, Hatogaya, Japan

[73] Assignee: Tokyo Eizai Laboratory Co., Ltd., Japan

[21] Appl. No.: 483,910

[22] Filed: Feb. 22, 1990

[30] Foreign Application Priority Data

Feb. 23, 1989 [JP] Japan ................. 1-21169[U]

[51] Int. Cl.$^5$ ............................................. A61F 3/00
[52] U.S. Cl. ................................... 128/80 C; 2/24
[58] Field of Search ................ 128/80 C, 80 R, 87 R; 2/22, 24; 272/119

[56] References Cited

U.S. PATENT DOCUMENTS

| 3,046,981 | 7/1962 | Biggs, Jr. et al. | 128/80 |
| 4,370,978 | 2/1983 | Palumbo | 128/80 C |
| 4,423,720 | 1/1984 | Meier et al. | 128/80 |
| 4,425,912 | 1/1984 | Harper | 128/80 C |
| 4,445,505 | 5/1984 | Labour et al. | 128/80 C |
| 4,506,661 | 3/1985 | Foster | 128/80 |
| 4,724,831 | 2/1988 | Huntjens | 128/80 C |
| 4,765,318 | 8/1988 | Tranberg et al. | 128/80 |
| 4,941,462 | 7/1990 | Lindberg | 128/80 C |

Primary Examiner—Richard J. Apley
Assistant Examiner—Jennifer L. Doyle
Attorney, Agent, or Firm—Haverstock, Garrett & Roberts

[57] ABSTRACT

A knee support comprising a main body for covering the knee joint and thigh and shank portions of a leg located above and below the knee joint, two straps respectively disposed extending laterally above and below the portion of the main body which corresponds to the patella, one end of each strap fixed to the main body while the free ends thereof are adapted to be detachably attached to the main body, and a patella pad fixed to the two straps so as to be brought into contact with a side portion of the patella when the support is mounted on a knee.

11 Claims, 3 Drawing Sheets

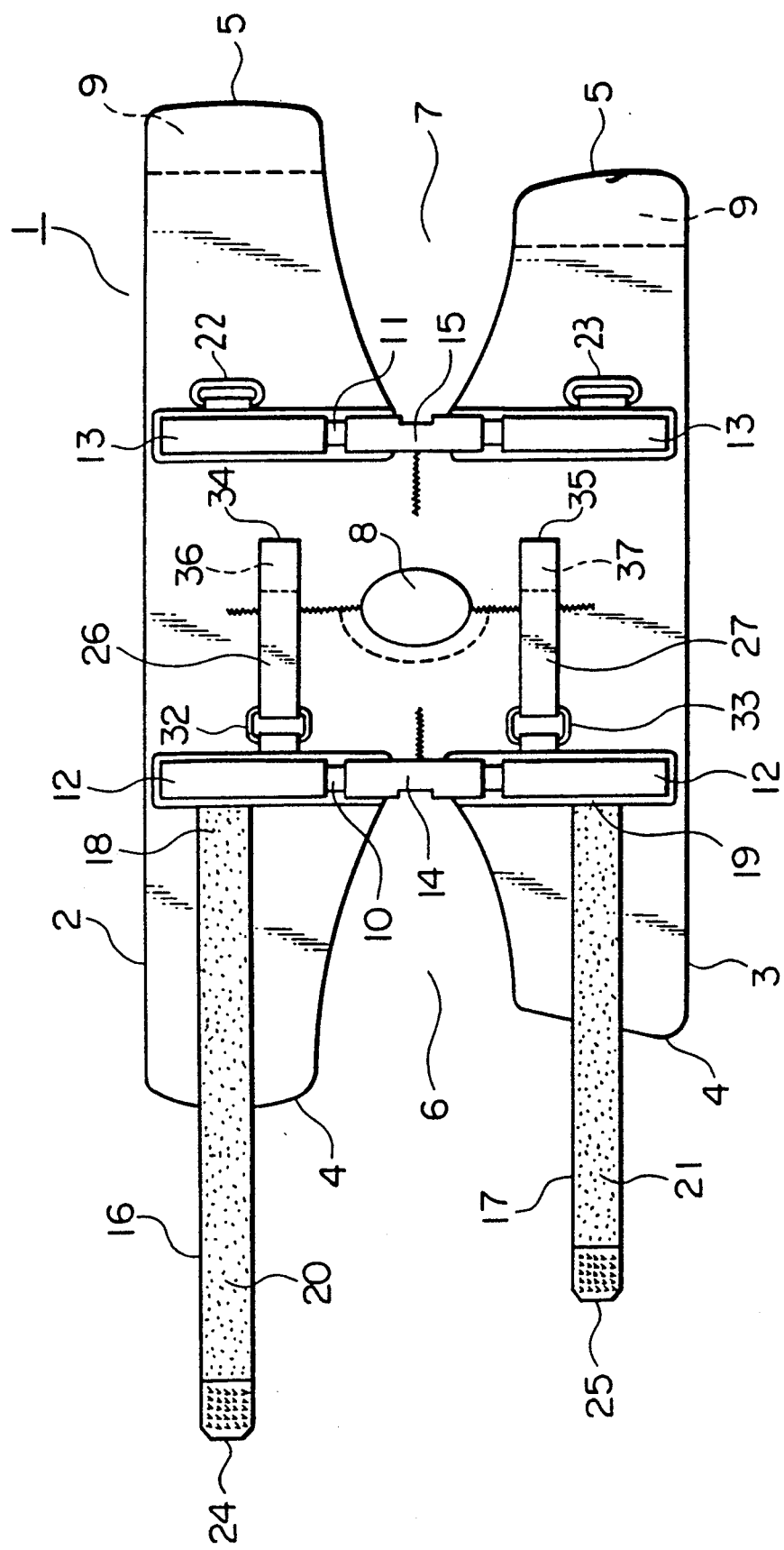

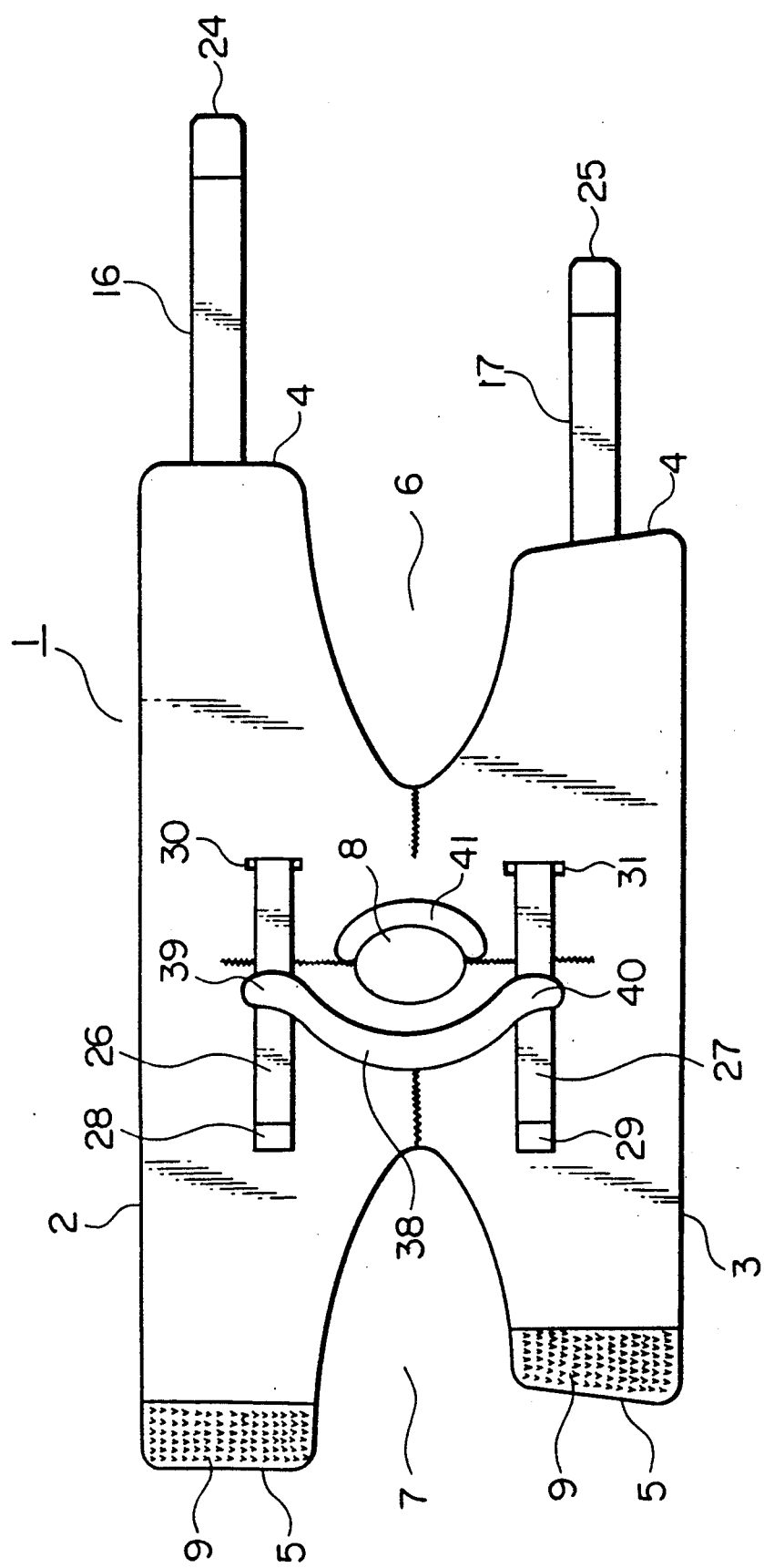

KNEE SUPPORT

DETAILED DESCRIPTION OF THE INVENTION

The present invention relates to a knee support for use for the prevention of knee trouble.

The patella slides over the patellar joint surface of the femoral condyle upon bending and stretching of the femorotibial or knee joint, but, in a case where a person has trouble or disfunction such as a patellar instability, an incomplete dislocation of the Patella, a dislocation of the patella, an anomaly in shape of the patella, or an anomalous support organ or system thereof, the patella may depart from the patellar joint surface of the femoral condyle, or a degenerative malacia of the patellar joint surface, i.e. patellar joint chondrosis, may be caused. There are various known devices for preventing the above-mentioned positional anomalies, but they are all of a construction type in which the knee joint portion is fixed or fastened by a main body composed of a material such as a cloth or the like, wherein a pad is attached to the inside portion of the main body which corresponds to the outer edge portion of the patella, and the portion of the main body corresponding to the whole periphery of the patella or a portion of the main body or the pad lying in the direction in which a dislocation tends to occur is made relatively thick so as to increase the pressure applied, whereby anomalous motion of the patella is controlled.

However, this type of construction has the following drawbacks;

1. Since the pad and the main body are formed as one integral structure, the pressure tends to become imbalanced depending on the diameter and shape of the knee joint surface.

2. Since the pad and the main body are formed as one integral structure, the direction in which the pressure is to be applied cannot be adjusted.

3. In a case where the main body cannot follow the stretching of the skin which occurs when the knee is bent and stretched, a deviation or departure is caused, as a result of which an inappropriate portion of the patella comes to be pressed.

It is an object of the present invention to provide a knee support used for prevention of an incomplete dislocation or a dislocation of the patella which is constructed in such a manner that the drawbacks of conventional knee supports described above are removed, the applied pressure and the direction in which the pressure acts can be adjusted, and the portion of the patella subjected to the pressure is allowed to vary hardly at all.

In accordance with the present invention, these objects can be achieved by a knee support comprising a main body for covering the knee joint Portion with the thigh and shank portions thereof located above and below the knee joint portion, two straps which are respectively disposed extending laterally above and below the portion of the main body which corresponds to the patella, while the free ends thereof being detachably attached to the main body, and a patella pad fixed to the two straps in such a manner as to be brought into contact with a side portion of the patella.

In accordance with the present invention, the main body is fixed onto the knee joint portion and the thigh and shank portions located above and below the knee joint portion in such a state that the patella pad is positioned at the side of the patella in the direction in which the patella tends to depart or deviate, and a suitable pull or pulling force is applied to the strap ends which are not fixed to the main body; and then the said ends are fixed to the main body, whereby the patella pad is closely adjoined to the side of the patella so as to apply a pressure to the patella from the direction in which the patella tends to depart. In this way, the occurance of an incomplete dislocation or a dislocation of the patella can be prevented.

BRIEF DESCRIPTION OF THE DRAWINGS

FIG. 1(a) and 1(b) are front and rear views, respectively, showing an embodiment of the present invention:

FIG. 2(a) and 2(b) are front and rear views, respectively, showing how the embodiment shown in FIG. 1 is actually mounted or put on.

FIGS. 1(a) and 1(b) are respectively front and rear views showing in opened state an embodiment of the knee support according to the present invention, of which FIG. 1(a) shows the front side or outside of the knee support, that is, the side opposite to the side to be contacted with the human body, while FIG. 1(b) shows the rear side or inside of the knee support, that is, the side contacted with the human body.

Figure 2A:
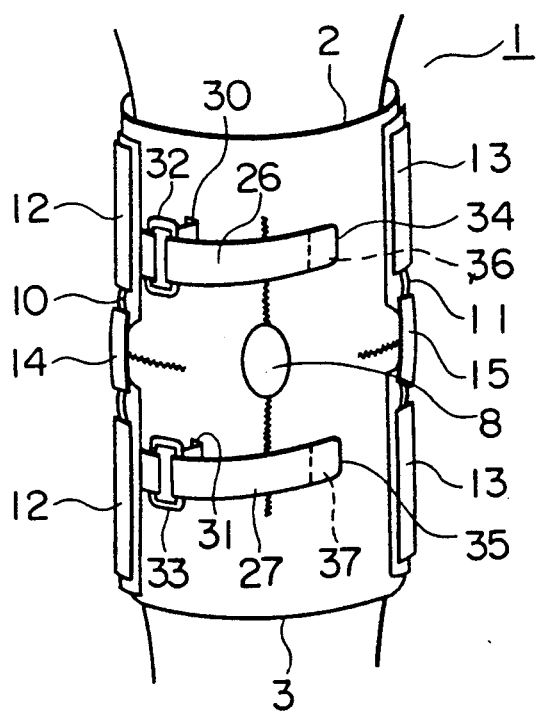

Numeral 1 denotes a main body comprising a resilient fabric, said main body 1 having a width and a length sufficient to cover the knee joint portion and the thigh and shank portions of the leg located above and below the knee joint portion. The main body has an upper side 2 which is formed somewhat longer than a lower side 3. In approximately the center of right side 4 and left side 5, lateral U-like recesses 6 and 7 are formed. In approximately the center of the main body 1 a hole 8 is formed. The portion of the main body 1 which lies above the recesses 6 and 7 and the hole 8 is adapted to cover the thigh portion of a leg, and the portion of the main body 1 which lies below the recesses 6 and 7 and the hole 8 is adapted to cover the shank portion, while the portion of the main body 1 in which the recesses 6 and 7 and the hole 8 are located is adapted to cover the knee joint with the recesses 6 and 7 being positioned to accommodate the popliteal fossa or "ham" at the back of the knee and the hole 8 being positioned to accommodate the patella. On the back surface of one side of the main body 1, e.g. the side 5, a Velcro or flat fastener 9 is provided. Stay covers 12 and 13 are provided on the front surface of the main body 1 at the right and left sides of the hole 8, the respective stay covers 12 and 13 containing stays 10 and 11 inside thereof. The stays 10 and 11 are of hinge type and the stay covers 12 and 13 are each divided into two parts so that one part will be located on the thigh Portion and the other on the shank portion, and protective covers 14 and 15 are fitted over the hinged portions of the stays 10 and 11 which are exPosed from the respective stay covers. To upper and lower portions of the outer side of one of the stay covers, e.g. the right stay cover 12, ends 18 and 19 of the fastening belts 16 and 17 are attached. These belts 16 and 17 extend laterally so that they will pass over the back sides of the thigh and shank portions when the knee support is put on or mounted. On the outer surfaces of the belts 16 and 17, flat fasteners 20 and 21 are provided. These belts 16 and 17 are arranged in such a manner that the free ends 24 and 25 thereof are inserted into ring-shaped fittings 22 and 23 mounted at upper and lower corresponding positions on the outer side of the other stay cover, e.g. the left stay cover 13 and folded back so as to be detachably connected to their own belts by means of the flat fasteners 20 and 21.

On the back surface of the main body 1, ends 28 and 29 of two straps 26 and 27 are fixed. Both straps 26 and 27 are disposed extending laterally above and below the hole 8 of the main body 1. The other ends 34 and 35 of the straps 26 and 27 are drawn out though slits 30 and 31 made in the main body 1, onto the front surface side of the main body 1, inserted into ring-shaped fittings 32 and 33 mounted to the stay cover 12, folded back, and detachably connected to the outer surface of the main body 1 by means of flat fasteners 36 and 37. To those portions of the straps 26 and 27 which extend on the back surface side of the main body 1, a patella pad 38 is fixed at positions 39 and 40 at one side, the left side in the embodiment shown, of the hole 8. In this case, a pad 41 is provided around the portion of the hole 8 which lies at the other side, i.e. the right side, at which the patella pad 38 is not present.

The main body 1 should desirably be sufficiently sized to have a width extending 10 to 20 cm above and below the patella. Suitable for use as the material of the main body 1 are a support fabric such as, e.g. an elastic tubular knitted fabric with rubber threads or spandex yarns incorporated therein, a foam material laminate product such as, e.g. neoprene rubber as a foam material, or a highly stretchable material such as a polyurethane sheet and a cloth or fabric which is stretchable.

As the material of the patella pad 38, a material such as a foam material e.g. a polyethylene, polyurethane or vinyl chloride foam, or a felt or a non-woven fabric which is agreeable to the touch and barely deformable is suitable. The thickness of the patella pad may be 5 to 20 mm, preferably 10 to 15 mm. Further, the patella pad, which extends along the shape of the side of the patella, should preferably have a circumferential length sufficient to cover 30 to 70% and, preferably 45 to 60%, of the entire circumferential length of the patella. This is because, if the coverage is too small, it may become hard for the wearer of the knee support to put forth his strength in an oblique direction, but if the coverage is too large, the patella pad may become hard to fit with the patella.

If the straps 26 and 27 are wholly formed of a stretchable material, the Pressure applied may become weak, and therefore, the greater part thereof is made of a non-stretchable material and only the tip portions thereof are made partially stretchable, which facilitates the fastening of the straps.

Figure 2B:
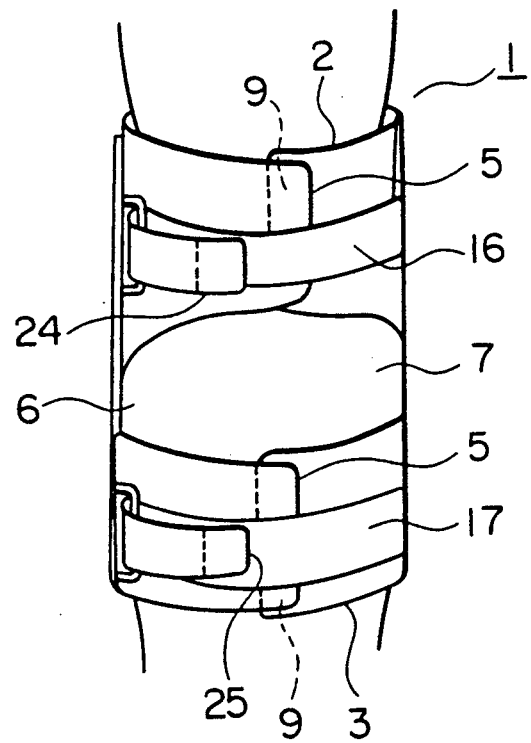

The method of putting on or mounting the knee support according to the present invention will now be described with reference to FIGS. 2(a) and 2(b). FIG. 2(a) is a front view and FIG. 2(b) is a rear view, both showing the knee support in mounted state.

When mounting, the support is placed with the rear side of the main body 1 in contact with the front side of the leg, so that the hole 8 is positioned on the patella, the upper side 2 on the anterior thigh and the lower side 3 on the anterior shank, with the stays 10 and 11 being positioned along the right and left sides of the knee extending from the thigh to the shank, respectively. Then, the right and left sides 4 and 5 are brought to overlap each other at the back of the leg with the side 5 overlapping side 4 so as to fasten the side 5 onto the main body 1 by means of flat fasteners 9. The recesses 6 and 7 in the right and left sides 4 and 5 are led by the superposition of the side 5 onto side 4 at the back of the knee to form an opening so as to enclose the popliteal fossa or "ham". Then the fastening belts 16 and 17 are passed behind the leg to insert the free ends 24 and 25 thereof into the ring-shaped fittings 22 and 23, to fold them back and to suitably pull them until they are fixed to their own belts by means of the flat fasteners 20 and 21, whereby the main body 1 is fixed with a suitable pressure being applied to the region around the patella.

Then, the free ends 34 and 35 of the straps 26 and 27 which have already been drawn out through the slits 30 and 31 onto the front side of the main body 1 are inserted into ring-shaped fittings 32 and 33 and folded back, whereby the pulling forces applied to the respective straps 26 and 27 are adjusted, and thus the direction and magnitude of the pressure applied by the patella pad 38 in contact with the patella are brought into a desirable state. Then the free ends 34 and 35 are fixed to the surface of the main body 1 by means of the flat fasteners 36 and 37.

Generally the inclination of the surface of the thigh bone which faces the patella becomes smaller toward the outer side thereof, so that a dislocation tends to occur, ordinarily, toward the outer side. In the case of the embodiment shown, the knee support is mounted or applied to the left leg, so that the patella pad produces a force directed inwardly; and thus a force acting in a direction opposite to the direction of a dislocation is applied to the patella, whereby the occurrence of the dislocation can be prevented. In the case where the knee support is applied to the right leg, it suffices if the straps and the patella pad are mounted in the opposite direction. In contrast, in the case of such a symptom that a dislocation tends to occur toward the inner side of the knee, the combination of straps and patella pad arranged so as to apply their forces at that side of the patella and in the opposite sense or direction should be employed.

The hole 8 of the main body 1 serves to prevent the main body 1 from being pulled, when the knee is bent, to apply a pressure to the patella. The recesses 6 and 7 provided in the main body 1 at the location which corresponds to the popliteal fossa portion are intended to reduce the occurrence of discomfort due to the fabric of the main body 1 which may be interposed in its slackened condition between the thigh and shank upon bending of the knee, but these recesses 6 and 7 need not necessarily be provided; the recesses may be replaced by a stretchable thin fabric if desired.

Further, the main body 1 need not necessarily be of an open type, but may be made in a tubular shape so that, by inserting his leg into it, the user can put it on.

In accordance with the present invention, the patella pad for applying a pressure to the patella is made independent of the main body and connected to the main body through straps, whereby it is ensured that, at any angle of the knee joint, the patella pad can be made to fit with the outer side edge or inner side edge of the patella, and further, the pressure applied to the patella can be freely adjusted. The undesirable variation of the portion of the side pressed by the patella pad due to the main body slipping out of position is reduced or avoided and moreover, due to the fact that the patella pad is supported by the two straps above and below the patella, the direction of pressure can also be adjusted; and thus, in accordance with the particular symptom of a patient it is possible to prevent the patella from being dislocated.

I claim:

1. A knee support comprising a main body having a knee portion for covering the knee joint and with thigh and shank portions located above and below the knee portion, said knee portion including a patella opening two straps which are respectively disposed extending in a lateral direction above and below said patella opening, one end of each of said straps being fixed to the inside of said main body, while the other ends thereof are adapted to pass through and be detachably attached to the outside of said main body, and a patella pad fixed to said two straps so as to abut one side of said patella opening.

2. The knee support according to claim 1 wherein the said straps are attached to the rear side of the main body and said patella pad is disposed on the rear side of the main body.

3. The knee support according to claim 1 wherein the main body comprises a flat stretchable fabric.

4. The knee support according to claim 3 wherein the stretchable fabric comprises an elastic knitted fabric, a laminated sheet product comprising a foam material or a stretchable plastic sheet material laminated to a stretchable fabric.

5. The knee support according to claim 1 wherein the main body comprises a knitted tube of stretchable fabric.

6. The knee support according to claim 1 wherein the patella pad comprises a foam material, a felt or non-woven fabric.

7. The knee support according to claim wherein the patella pad has a thickness of from about 5 to about 20 mm.

8. The knee support according to claim 1 wherein the patella pad abutting one side of the patella opening has a length sufficient to contact from 30 to 70% of the circumferential length of a patella when said patella opening is positioned thereabout.

9. The knee support according to claim 1 wherein the patella pad can be positioned to come in contact with either side of a patella by the disposition of said straps when said patella opening is positioned thereabout.

10. The knee support according to claim 1 including a second pad fixed to the main body so as to abut the side of the patella opening not abutted by the patella pad fixed to the said straps.

11. In a knee support comprising a main body having a knee portion for covering a knee joint with thigh and shank portions above and below the knee portion, said knee portion including a patella opening hinged stays on the outer surface of the main body for positioning at the right and left sides of a knee joint and means for mounting and adjusting said main body on a knee joint and the thigh and shank portions on a leg, the improvement comprising two straps respectively disposed extending laterally above and below said patella opening, one end of each of said straps being fixed to the inner surface of said main body, while the other ends thereof being adapted to pass to the outer side of said main body and to be detachably attached thereto, and a patella pad fixed to said straps at the inner side of said main body so as to adjustably abut one side of the patella opening.

* * * * *

UNITED STATES PATENT AND TRADEMARK OFFICE
CERTIFICATE OF CORRECTION

PATENT NO. : 5,024,216
DATED : June 18, 1991
INVENTOR(S) : Katuaki Shiono

It is certified that error appears in the above-identified patent and that said Letters Patent is hereby corrected as shown below:

Column 1, line 12, "Patella" should be --patella--

Column 1, line 56, "Portion" should be --portion--

Column 2, line 38, "i$" should be --is--

Column 2, line 55, "Portion" should be --portion--

Column 2, line 58, "exPosed" should be --exposed--

Column 3, line 47, "Pressure" should be --pressure--

Column 6, line 1, after "claim" insert --1--

Signed and Sealed this

Twenty-second Day of September, 1992

Attest:

DOUGLAS B. COMER

*Attesting Officer*     *Acting Commissioner of Patents and Trademarks*